(12) United States Patent
Horiba et al.

(10) Patent No.: US 9,023,799 B2
(45) Date of Patent: May 5, 2015

(54) METHOD TO REDUCE LOSS OF CARDIAC FUNCTION FOLLOWING ISCHEMIA/REPERFUSION

(75) Inventors: Mitsuru Horiba, Aichi (JP); Itsuo Kodama, Aichi (JP); Takashi Muramatsu, Aichi (JP); Kenji Kadomatsu, Aichi (JP)

(73) Assignee: Cellmid Limited, Sydney New South Wales (AU)

( * ) Notice: Subject to any disclaimer, the term of this patent is extended or adjusted under 35 U.S.C. 154(b) by 1888 days.

(21) Appl. No.: 11/720,983

(22) PCT Filed: Dec. 6, 2005

(86) PCT No.: PCT/JP2005/022354
§ 371 (c)(1),
(2), (4) Date: Sep. 1, 2009

(87) PCT Pub. No.: WO2006/062087
PCT Pub. Date: Jun. 15, 2006

(65) Prior Publication Data
US 2010/0056437 A1 Mar. 4, 2010

(30) Foreign Application Priority Data

Dec. 6, 2004 (JP) ................................. 2004-352513
Jun. 27, 2005 (JP) ................................. 2005-187420

(51) Int. Cl.
*A61K 38/00* (2006.01)
*A61K 38/16* (2006.01)
*A61K 38/18* (2006.01)

(52) U.S. Cl.
CPC ...................... *A61K 38/18* (2013.01)

(58) Field of Classification Search
CPC ... A61K 38/57; A61K 2300/00; A61K 38/00; A61K 38/16; Y10S 977/904
See application file for complete search history.

(56) References Cited

U.S. PATENT DOCUMENTS

| 6,383,480 | B1 * | 5/2002 | Kikuchi et al. ............... 424/85.1 |
| 2003/0185794 | A1 * | 10/2003 | Colley .......................... 424/85.1 |
| 2004/0219129 | A1 | 11/2004 | Yoshida et al. |
| 2005/0079151 | A1 | 4/2005 | Ikematsu et al. |
| 2006/0216709 | A1 * | 9/2006 | Levita et al. ........................ 435/6 |

FOREIGN PATENT DOCUMENTS

| EP | 1057489 A1 | 6/2000 |
| EP | 1097717 A1 | 9/2001 |
| JP | 8-27021 A | 1/1996 |
| JP | 2002-512200 A | 4/2002 |
| JP | 2005-68122 | 3/2005 |
| WO | WO 99/16463 A1 | 4/1999 |
| WO | WO 99/53943 A2 | 10/1999 |
| WO | WO 00/02578 A1 | 1/2000 |
| WO | WO 2007/055397 | * 5/2007 ............. A61K 38/00 |

OTHER PUBLICATIONS http://www.wisegeek.com/what-is-cardiopathy.htm, downloaded Dec. 20, 2010.*
Horiba et al., "Midkine Plays a Protective Role Against Cardiac Ischemia/reperfusion Injury through a Reduction of Apoptotic Reaction" *Circulation Supplement III*, Oct. 26, 2004, pp. 106, vol. 110, No. 17.
Yaoita et al., "Apoptosis in relevant clinical situations: contribution of apoptosis in myocardial infarction" *Cardivascular Research*, 2000, pp. 630-641, vol. 45, No. 3.
Horiba et al., "Cardioprotective Action of Midkine Against Ischemia/ Reperfusion Injury: Functional, Morphological and Molecular Biological Evidence" Journal of Cardiac Failure (2004) 10(5):S151.
Jones et al., "Pretreatment with simvastatin attenuates myocardial dysfunction after ischemia and chronic reperfusion" Arterioscler. Thromb. Vasc. Biol. (2001) 21:2059-2064.
Kaeffer et al., "Preconditioning prevents chronic reperfusion-induced coronary endothelial dysfunction in rats" American Journal of Physiology (1996) 271:H842-H849.
Laude et al., "Coronary endothelial dysfunction after ischemia and reperfusion: a new therapeutic target?" Brazilian Journal of Medical and Biological Research (2001) 34:1-7.
Pearson et al., "Long-term Impairment of Endothelium-Dependent Relaxations to Aggregating Platelets After Reperfusion Injury in Canine Coronary Arteries" Circulation (1990) 81(6):1921-1927.
Shimokawa et al., "Porcine Coronary Arteries with Regenerated Endothelium-Dependent Responsiveness to Aggregating Platelets and Serotonin" Circulation Research (1987) 61(2):256-270.

* cited by examiner

*Primary Examiner* — Shulamith H Shafer
(74) *Attorney, Agent, or Firm* — Morrison & Foerster LLP

(57) ABSTRACT

A method to treat the chronic stage of heart injury after ischemia or reperfusion by administering Midkine to a subject in need of such treatment is described.

7 Claims, 15 Drawing Sheets

FIG. 10

| | n | Heart/body weight (% by weight) | Survival rate (%) |
|---|---|---|---|
| Control | 11 | 5.7 % | 84 % |
| MK (−/−) | 12 | 6.2 % | 55 % |
| MK (−/−) + MK Protein | 8 | 5.8 % | 87.5 % |

<Wild-type>

<MK-knockout>

<MK-knockout+MK>

SEQUENCE LISTING

<160> NUMBER OF SEQ ID NOS: 1

<210> SEQ ID NO 1
<211> LENGTH: 562
<212> TYPE: DNA
<213> ORGANISM: Homo sapiens
<220> FEATURE:
<221> NAME/KEY: CDS
<222> LOCATION: (1)..(432)

```
<400> SEQUENCE: 1 atg cag cac cga ggc ttc ctc ctc ctc acc ctc ctc gcc ctg ctg gcg      48
Met Gln His Arg Gly Phe Leu Leu Leu Thr Leu Leu Ala Leu Leu Ala
1               5                   10                  15 ctc acc tcc gcg gtc gcc aaa aag aaa gat aag gtg aag aag ggc ggc      96
Leu Thr Ser Ala Val Ala Lys Lys Lys Asp Lys Val Lys Lys Gly Gly
                20                  25                  30 ccg ggg agc gag tgc gct gag tgg gcc tgg ggg ccc tgc acc ccc agc     144
Pro Gly Ser Glu Cys Ala Glu Trp Ala Trp Gly Pro Cys Thr Pro Ser
            35                  40                  45 agc aag gat tgc ggc gtg ggt ttc cgc gag ggc acc tgc ggg gcc cag     192
Ser Lys Asp Cys Gly Val Gly Phe Arg Glu Gly Thr Cys Gly Ala Gln
        50                  55                  60 acc cag cgc atc cgg tgc agg gtg ccc tgc aac tgg aag aag gag ttt     240
Thr Gln Arg Ile Arg Cys Arg Val Pro Cys Asn Trp Lys Lys Glu Phe
65                  70                  75                  80 gga gcc gac tgc aag tac aag ttt gag aac tgg ggt gcg tgt gat ggg     288
Gly Ala Asp Cys Lys Tyr Lys Phe Glu Asn Trp Gly Ala Cys Asp Gly
                85                  90                  95 ggc aca ggc acc aaa gtc cgc caa ggc acc ctg aag aag gcg cgc tac     336
Gly Thr Gly Thr Lys Val Arg Gln Gly Thr Leu Lys Lys Ala Arg Tyr
            100                 105                 110 aat gct cag tgc cag gag acc atc cgc gtc acc aag ccc tgc acc ccc     384
Asn Ala Gln Cys Gln Glu Thr Ile Arg Val Thr Lys Pro Cys Thr Pro
        115                 120                 125 aag acc aaa gca aag gcc aaa gcc aag aaa ggg aag gga aag gac tag     432
Lys Thr Lys Ala Lys Ala Lys Ala Lys Lys Gly Lys Gly Lys Asp
    130                 135                 140 acgccaagcc tggatgccaa ggagccctg gtgtcacatg gggcctggcc cacgccctcc    492
ctctcccagg cccgagatgt gacccaccag tgccttctgt ctgctcgtta gctttaatca   552
atcatgcccc                                                          562
```

METHOD TO REDUCE LOSS OF CARDIAC FUNCTION FOLLOWING ISCHEMIA/REPERFUSION

CROSS-REFERENCE TO RELATED APPLICATION

This application is the National Stage of International Application Number PCT/JP2005/022354, filed Dec. 6, 2005, which is hereby incorporated by reference herein in its entirety, including any figures, tables, nucleic acid sequences, amino acid sequences, or drawings.

TECHNICAL FIELD

The present invention relates to pharmaceutical compositions for treating or preventing myocardial damage, which comprise Midkine as an active ingredient, and pharmaceutical compositions for treating or preventing heart failure, which comprise Midkine as an active ingredient.

BACKGROUND ART

A number of previous studies have indicated that cardiomyocyte death characteristic of apoptosis occurs in response to ischemia/reperfusion (I/R). These have also reported the pathology of cardiopathies observed under such conditions (Bialik, S. et al., 1997; Gottlieb, R. A. et al., 1994; Maulik, N. et al., 1999; Tanaka, M. et al., 1994). Since apoptosis occurs within 24 hours after ischemia/reperfusion and is accompanied by a massive loss of cardiomyocytes, it considerably increases the risk of developing cardiac dysfunctions (Colucci, W. S., 1996). Therefore, if cardiomyocyte apoptotic death could be inhibited, ischemia/reperfusion-based cardiac symptoms and dysfunctions including myocardial damages such as myocardial infarction and angina pectoris could be reduced. Recently, the importance of apoptosis in cell death following reperfusion was demonstrated, and several methods and strategies for inhibiting apoptotic cell death have been proposed. These methods include pharmaceutical methods, growth factor-mediated methods, and genetic interference (Eefting, F. et al., 2004).

Midkine (MK) is a 13 kDa heparin-binding growth factor, which is rich in basic amino acids and cysteines (Kadomatsu, K. et al., 1988; Tomomura, M. et al., 1990). Since the amino acid sequences of MK and pleiotrophin/heparin-binding growth-associated molecule (PTN/HB-GAM) are 50% homologous, these molecules can be distinguished from molecules such as fibroblast growth factors (FGFs), and hepatocyte growth factors (HGFs) (Li, Y. S. et al., 1990; Merenmies, J. et al., 1990; Muramatsu, T., 1993). MK expression in adult tissues is strictly limited, and in mice, this proteinaceous factor is expressed only in the kidneys and the uterus at high concentrations. MK and PTN/HB-GAM both have neurotrophic activity, and may be associated with nerve growth and tumor growth. In cultured nerve cells (neurons), MK inhibits caspase-dependent apoptosis via activation of ERK, a type of mitogen-activated protein kinase (Owada, K. et al., 1999). Another effect of MK is to protect cells from damage by enhancing the expression of Bcl-2 (Qi, M. et al., 2000).

Myocardial damages such as ischemic heart disease and dilated cardiomyopathy are fatal diseases. Even if life could be sustained, heart failure is very likely to occur and the quality of life will be considerably restricted. Particularly in severe heart failure, the only effective method at present is heart surgery that has donor availability and histocompatibility issues, and there are no other effective radical methods of treatment.

Ikematsu et al. have previously proposed therapeutic agents or preventive agents for ischemic diseases, which comprise MK as an active ingredient (see Patent Document 1).

[Patent Document 1] WO99/16463 pamphlet

DISCLOSURE OF THE INVENTION

An objective of the present invention is to provide pharmaceutical compositions for treating or preventing myocardial damage or heart failure. A further objective of the present invention is to provide pharmaceutical compositions for treating or preventing myocardial damage or heart failure without performing heart surgery, a procedure with donor availability and histocompatibility issues.

The present inventors investigated whether MK is activated by a clinically related pathological stimulus in the heart of wild-type mice. The present inventors also compared myocardial injury after ischemia/reperfusion in wild-type mice and MK-deficient mice to confirm the effects and functions of MK. The present inventors further investigated whether MK administration prevents cardiomyocyte apoptosis in mouse models (in vivo) and in cultured cardiomyocytes (in vitro), respectively, and went on to discover that MK is an important factor for preventing cardiomyocyte apoptosis both in vivo and in vitro. Furthermore, the present inventors found that MK administration reduces myocardial injury following ischemic injury, and completed the present invention.

More specifically, the present invention provides pharmaceutical compositions for treating myocardial damage, which comprise Midkine as an active ingredient. The present invention also provides pharmaceutical compositions for preventing myocardial damage, which comprise Midkine as an active ingredient. The present invention additionally provides pharmaceutical compositions for treating heart failure, which comprise Midkine as an active ingredient. Furthermore, the present invention provides pharmaceutical compositions for preventing heart failure, which comprise Midkine as an active ingredient.

The present invention further provides methods for treating myocardial damage, in which the methods comprise administering Midkine. The present invention also provides methods for preventing myocardial damage, in which the methods comprise administering Midkine. The present invention additionally provides methods for treating heart failure, in which the methods comprise administering Midkine. Furthermore, the present invention provides methods for preventing heart failure, in which the methods comprise administering Midkine.

The present invention further provides uses of Midkine for producing pharmaceutical agents for treating myocardial damage. The present invention also provides uses of Midkine for producing pharmaceutical agents for preventing myocardial damage. The present invention additionally provides uses of Midkine for producing pharmaceutical agents for treating heart failure. Furthermore, the present invention provides uses of Midkine for producing pharmaceutical agents for preventing heart failure.

The present invention further provides kits that comprise a pharmaceutical composition comprising Midkine as an active ingredient and instructions for using the composition to treat patients with myocardial damage. The present invention also provides kits that comprise a pharmaceutical composition comprising Midkine as an active ingredient and instructions for using the composition to prevent myocardial damage. The present invention additionally provides kits that comprise a pharmaceutical composition comprising Midkine as an active ingredient and instructions for using the composition to treat patients with heart failure. Furthermore, the present invention provides kits that comprise a pharmaceutical composition comprising Midkine as an active ingredient and instructions for using the composition to prevent heart failure. The instructions included in the kits may be described on the outside of packages containing the kits.

BRIEF DESCRIPTION OF THE DRAWINGS

FIG. 1 (a) shows the result of a 15% SDS-PAGE and Western blotting on proteins extracted from Mdk$^{+/+}$ mouse hearts. FIG. 1 (b) shows the intensities of the obtained bands quantified with a densitometry. n=5, and *P<0.01.

FIG. 7(a) is a graph showing the anti-apoptotic effect of MK protein when cultured cardiomyocytes were subjected to hypoxia-reoxygenation (H/R). The effect is shown as quantitative DNA fragmentation data determined by ELISA.

FIG. 8 (bottom) is an electropherogram showing the activation of ERK-1/2 by MK in cultured cardiomyocytes, in which anti-phospho-ERK-1/2 antibody was used for detection.

FIG. 10 shows the mortality rates and the heart/body weight ratios two weeks after reperfusion for chronic stage mouse models. In order from the top: for Mdk$^{+/+}$ mice, Mdk$^{-/-}$ mice, and Mdk$^{-/-}$ mice to which MK protein was continuously administered. n=11, 12, and 8, respectively.

BEST MODE FOR CARRYING OUT THE INVENTION

Figure 1:
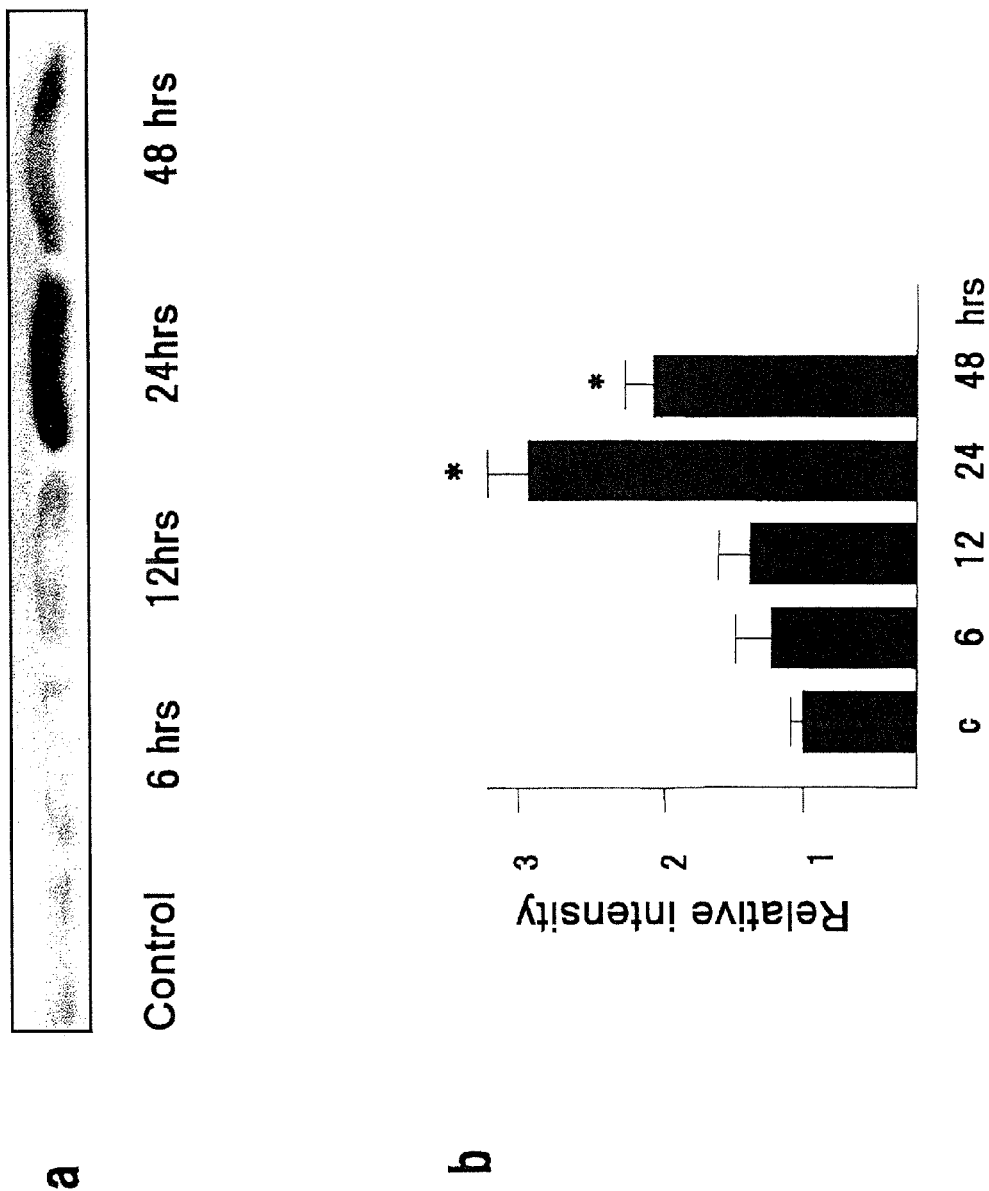
FIG. 1 shows the time course of MK expression in wild-type mouse hearts after ischemia/reperfusion.

The present invention provides pharmaceutical compositions for treating or preventing myocardial damage or heart failure, which comprises Midkine (MK) as an active ingredient.

MK comprised in a pharmaceutical composition as an active ingredient may preferably be an MK polypeptide encoded by the DNA of SEQ ID NO: 1; however, it is not limited thereto, and includes polypeptides showing therapeutic or preventive effects against myocardial damage or heart failure, which comprise an amino acid sequence with one or more amino acid substitutions, deletions, insertions, or additions in the amino acid sequence of the MK polypeptide encoded by the DNA of SEQ ID NO: 1.

Whether a polypeptide shows therapeutic or preventive effects against myocardial damage or heart failure can be readily confirmed by one skilled in the art, for example, by "evaluation of the ischemic area at risk and infarct size" or "immunohistochemical methods".

A polypeptide functionally equivalent to the above-mentioned MK usually has an amino acid sequence highly homologous to MK. "Highly homologous" usually refers to having a sequence identity of at least 50% or more, preferably 75% or more, even more preferably 85% or more, and yet even more preferably 95% or more at the amino acid level. Amino acid sequence and nucleotide sequence identities can be determined by algorithms such as BLAST (Proc. Natl. Acad. Sci. USA 90:5873-5877, 1993).

Polypeptides that comprise an amino acid sequence with one or more amino acid mutations in the amino acid sequence of MK, and are functionally equivalent to this polypeptide are also encompassed in the present invention. The number of mutated amino acids is usually 30 amino acids or less, preferably 15 amino acids or less, more preferably five amino acids or less (for example, three amino acids or less), and even more preferably two amino acids or less. The amino acids are preferably mutated to other amino acid residues that allow the properties of the amino acid side chains to be conserved. Examples of amino acid side chain properties include: hydrophobic amino acids (A, I, L, M, F, P, W, Y, and V), hydrophilic amino acids (R, D, N, C, E, Q, G, H, K, S, and T), and amino acids comprising the following side chains: aliphatic side chains (G, A, V, L, I, and P), hydroxyl-containing side chains (S, T, and Y), sulfur-containing side chains (C and M), carboxylic acid- and amide-containing side chains (D, N, E, and Q), base-containing side chains (R, K, and H), and aromatic-containing side chains (H, F, Y, and W) (amino acids are represented by one-letter codes in parentheses).

Next, the methods of the present invention will be described in detail.

<Preparation of Animal (Mouse) Models>

Mice that were used in this experiment were those genetically incapable of producing MK (Mdk$^{-/-}$ mice), which were bred by Nakamura et al. (Genes Cells 3:811-822, 1998). Both wild-type mice (Mdk$^{+/+}$ mice) and Mdk$^{-/-}$ mice incapable of producing MK have the C57BL/6 genetic background, and mice of the same age were used for the experiment. These mice were fed an ordinary rodent diet. The mice were anesthetized with pentobarbital (100 mg/kg, i.p.), and life was sustained using an artificial respirator (model SN-480-7). After open-chest surgery, the left anterior descending coronary artery (LAD) was ligated with a PE-10 tube. Myocardial ischemia was confirmed by whitening of the left ventricle (LV). After one hour of ligation, the ligature was removed and the blood flow resumed.

For acute stage models, MK protein was infused directly into the cardiac muscle at the time of reperfusion. Without particular limitation, the amount of infused MK protein is usually 0.01 to 1 μg, preferably 0.05 to 0.8 μg, and more preferably 0.1 to 0.5 μg. Herein, 20 μl of MK protein solution (10 μg/ml) dissolved in physiological saline was directly injected into the anterior left ventricular wall using a microsyringe having a 30 G needle. 24 hours after reperfusion, cardiac function was evaluated by cardiac ultrasonography (echocardiography), and the lesion area, histopathological changes, and expression of various proteins associated with the lesion were compared and examined.

For chronic stage models, their conditions were followed up for two weeks after reperfusion. At the beginning of observation, the Mdk$^{-/-}$ mice were divided into two groups, and MK protein was administered continuously to one group. Methods for continuous administration of MK protein may include the method of subcutaneously implanting a controlled release capsule containing the MK protein at the time of ischemia/reperfusion, and the method of administering an adenovirus carrying the MK gene at the time of reperfusion so that the virus is infused into the coronary vessel, but herein, MK protein was directly infused using an osmotic pressure pump. More specifically, ALZET micro-osmotic pump (Model 1002) loaded with 90 μl of MK protein solution (0.8 mg/ml) was subcutaneously implanted in the abdomen, and the protein was continuously administered by osmotic pressure. Although there were no definite data comparing and examining the optimum MK protein level for administration to mice, the administration was performed according to a method that had been disclosed by the present inventors (Horiba, M. et al.: J. Clin. Invest. 105:489-495, 2000). During the follow-up examination, the cardiac function and morphological changes such as changes in wall thickness and lumen diameter were observed over time by cardiac ultrasonography (echocardiography). After the follow-up examination, the lesion area, histopathologic changes, and expression of various proteins associated with the lesion were compared and examined as in the acute stage models.

<Evaluation of the Area at Risk and Infarct Size>

As described above, mice were anesthetized and open-chest surgery was carried out. Reocclusion of the left anterior descending coronary artery (LAD) was followed by injection of 0.2 ml of 5% Evans blue into the void of the left ventricle for counter staining. The left ventricle was sliced into 5 sections, and the ischemic areas at risk of the left ventricle were stained using triphenyltetrazolium chloride (TTC). The areas of the infarct region (lightly colored region), area at risk (the region that is not blue), and the entire left ventricle were individually determined using a computer. Serum CPK determination was outsourced to an external institution (SRL).

<Ultrasonography (Echocardiography)>

Echocardiography was performed using Nemio 20 (Toshiba). The mice were lightly anesthetized with ether, and laid on their backs on a warming pad. The function of the left ventricle was measured under consciousness. A 12-MHz converter was attached to the left half of the chest, and the M-mode image of the heart was recorded. An observer, who had not been told the genotype of the mice, analyzed the obtained data.

<MK Protein and Antibodies>

An expression vector for yeast (*Pichia pastoris* GS115), in which a cDNA fragment comprising the open reading frame of human MK was introduced into pHIL-D4, has already been constructed. After transfection of this expression vector into yeast, selection using histidine and G418 was conducted. The human MK protein was purified from yeast by anion exchange chromatography and affinity chromatography on a heparin column. The purified product exhibited neurotrophic activity comparable to that of mouse MK protein obtained from L cells. Antibodies against bacteria-produced mouse MK were raised by injecting the purified protein into rabbits, and purified by a combination of affinity chromatography on protein A and MK columns. The obtained antibodies were specific to MK and did not react with PTN/HB-GAM.

<Western Blotting>

Approximately 10 mg of the proteins extracted from the mouse hearts was separated by 15% SDS-PAGE. MK protein was detected with anti-mouse MK antibody using ECL kit (Amersham). The intensities of the bands were analyzed with a densitometry. In the in vitro experiment, cultured cardiomyocytes were lysed in an SDS sample buffer, the cell lysate was separated by 12% SDS-PAGE, and then Western blotting and band analysis were performed using a method similar to that described above. However, the antibodies used were anti-Bcl-2 antibody (Santa Cruz Biotechnology) or anti-ERK1/2 antibody and anti-diphosphorylated ERK1/2 antibody (Sigma).

<Histopathological Methods>

Mouse hearts were fixed in 4% paraformaldehyde, embedded in paraffin, and sliced into 5 μm thick sections. Hematoxylin-eosin staining was carried out on these 5 μm thick paraffin sections to evaluate the lesions.

<Immunohistochemical Methods>

Immunostaining of 5 μm thick paraffin sections obtained by a method same as that described above was performed according to the method described in Biochem. Biophys. Res. Commun., 192:246-251, 1993. In addition to incubation with unlabeled sheep anti-rat IgG (Jackson Laboratory) as the second antibody, biotinylated-tyramide and streptavidin-horseradish peroxidase (NEN Life Science Products) were added to the incubation mixture to enhance the reaction.

<Cell Culture>

Primary cultures of cardiomyocytes from neonatal mouse ventricles were prepared from one-day old ICR mice according to the manual on Neonatal Cardiomyocyte Isolation System (USA). More specifically, ventricular sections were incubated while stirring at 37° C. for 15 minutes in $Ca^{++}$ and $Mg^{++}$-free Hanks' balanced salt solution containing 100 U/ml collagenase, and then a cell suspension was collected. The separated cells were cultured using M199 medium (GIBCO BRL) containing 10% fetal bovine serum, 5 μM cytosine arabinoside, 50 U/ml penicillin, and 50 μg/ml streptomycin in a humid carbon dioxide gas incubator at 37° C.

To investigate resistance against apoptosis, cardiomyocytes were incubated under an anaerobic atmosphere of 5% carbon dioxide gas and 95% nitrogen gas at 37° C. for 6 hours, and a hypoxic state was produced. Next, the medium was exchanged for a medium containing 0.5% fetal bovine serum, without MK protein or supplemented with 100 ng/ml of MK protein, and oxygenation was resumed. Cells were collected 18 hours after reoxygenation. For ERK analysis, the cardiomyocytes were serum starved for 24 hours and then treated with 100 ng/ml of MK protein for 30 minutes.

<Apoptosis Determination>

Apoptosis was detected by TUNEL assay. Deparaffinated sections or cultured cardiomyocytes fixed with 4% paraformaldehyde in PBS were incubated with a proteinase, and the DNA fragments were labeled with fluorescein-conjugated dUTP using TdT (Roche Diagnostics). The concentration of the nuclei was manually determined by counting the number of nuclei stained with Hoechst 33342 (observing five fields at 40× magnification), and the ratio of TUNEL-positive cells relative to the Hoechst 33342-stained nuclei was calculated.

Apoptosis was detected by using a Cell Death Detection ELISA Kit (Roche Diagnostics) on DNA fragments of cultured cardiomyocytes and quantifying the cytosolic oligonucleosome-bound DNA. More specifically, the cytosolic fraction of cardiomyocytes was used as the antigen for sandwich ELISA (in which the primary antibody was an anti-histone antibody bound to a microtiter plate, and the secondary antibody was a peroxidase-conjugated anti-DNA antibody).

<Statistical Analysis>

All values are represented as mean±standard deviation. Student's t-test was used for statistical analyses among groups. $P<0.05$ was defined as "significantly different".

All prior art literature cited herein are incorporated by reference.

EXAMPLES

Herein below, the present invention will be specifically described using Examples and referring to Figures, but it is not to be construed as being limited thereto.

Example 1

Expression Pattern of MK Protein in Wild-Type Mouse Heart

The time course of MK expression in wild-type mouse hearts after ischemia/reperfusion is shown in FIG. 1. FIG. 1 (a) is an electropherogram obtained by separating 10 mg of the protein extracted from $Mdk^{+/+}$ mouse hearts through 15% SDS-PAGE and then performing Western blotting; and (b) is a graph showing the intensities of the obtained bands which were quantified with a densitometry. This shows that MK expression in the control is weak, increases with time after ischemia/reperfusion (I/R), and reaches a maximum at 24 hours after I/R, and the increased expression continues up to 48 hours after I/R.

MK localization was analyzed immunohistochemically in the control cardiac sections of $Mdk^{+/+}$ mouse hearts and the cardiac sections 24 hours after ischemia/reperfusion (micrographs not shown). In the control cardiac sections, MK protein appeared spread out and pale, but in the cardiac sections 24 hours after ischemia/reperfusion, a strong level of MK protein was found around the infarct area. When the micrographs were enlarged, MK protein clearly appeared different in the border between the infarct area and the peri-infarct region, and was expressed mainly in the membrane of cardiomyocytes in the peri-infarct region (enlarged micrographs not shown).

Example 2

Comparison of Myocardial Injuries After Ischemia/Reperfusion in Wild-Type Mice and in $Mdk^{-/-}$ Mice Myocardial injuries after ischemia/reperfusion were compared using the acute stage $Mdk^{+/+}$ mouse and $Mdk^{-/-}$ mouse models. In the left ventricular sections, tissues that turned blue by Evans blue staining were identified as areas not at risk, and regions in areas at risk that turned red by TTC staining were identified as tissues that were still alive (micrographs not shown). The regions that were not stained by either Evans blue or by TTC appeared whitish, and this was identified as the infarct region.

Figure 2:
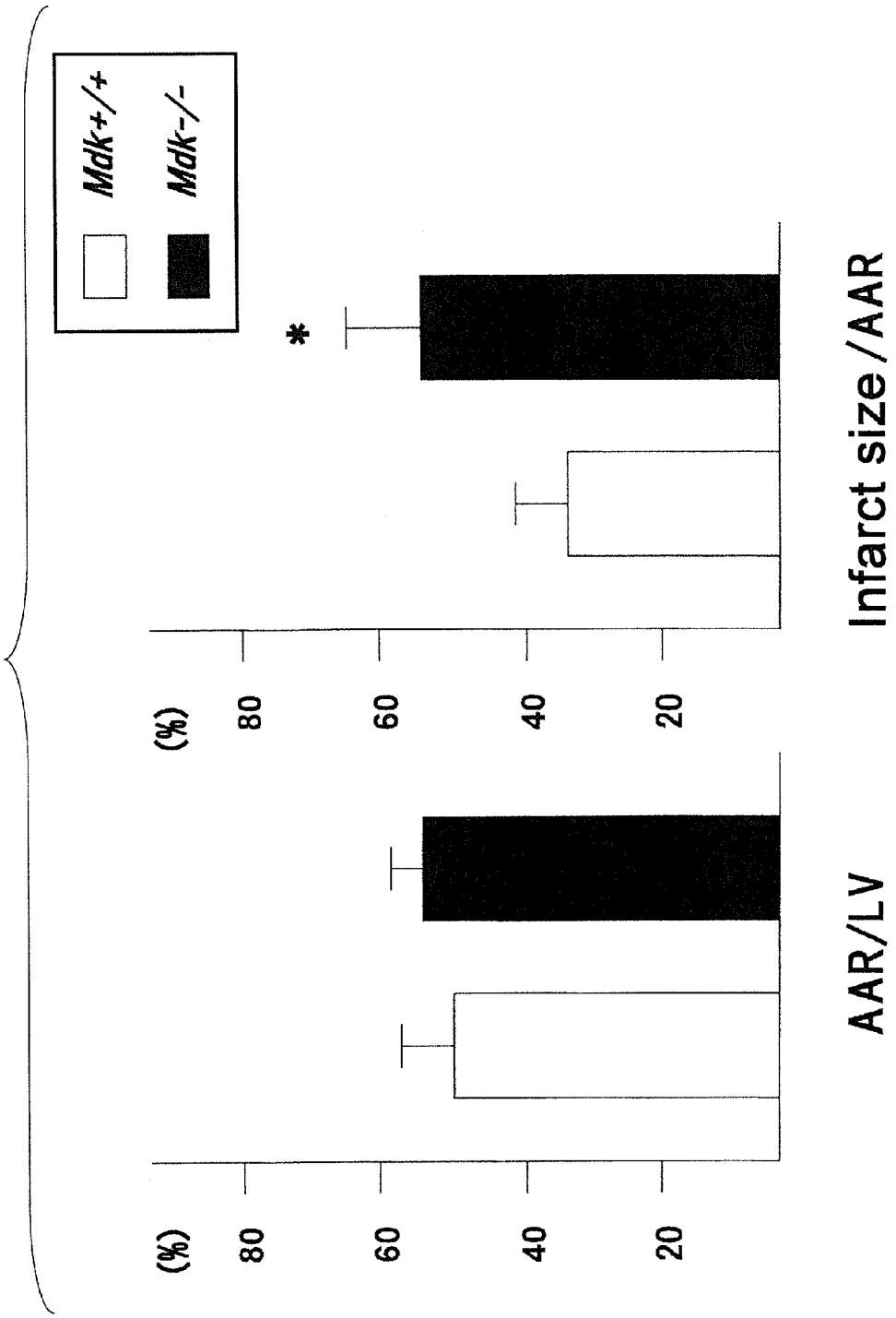
FIG. 2 shows graphs indicating the result of a quantitative analysis of the left ventricular area at risk (AAR) after ischemia/reperfusion. The graph on the left shows the percentages of the infarct area of the left ventricle (LV) relative to the left ventricular area at risk (AAR), and the right shows the percentages of the infarct size (white necrotic region) in the AAR. n=8, respectively; and *P<0.05.

In FIG. 2, the left graph shows percentages of the infarct areas of the left ventricle (LV) relative to the ischemic left ventricular areas at risk (AAR); and the right graph shows percentages of the infarct size (the white necrotic region) in the AAR. Comparison of $Mdk^{+/+}$ mice and $Mdk^{-/-}$ mice showed that although areas at risk (AAR) for both mice are similar, the infarct size in the AAR was significantly larger in $Mdk^{-/-}$ mice than in $Mdk^{+/+}$ mice.

Figure 3:
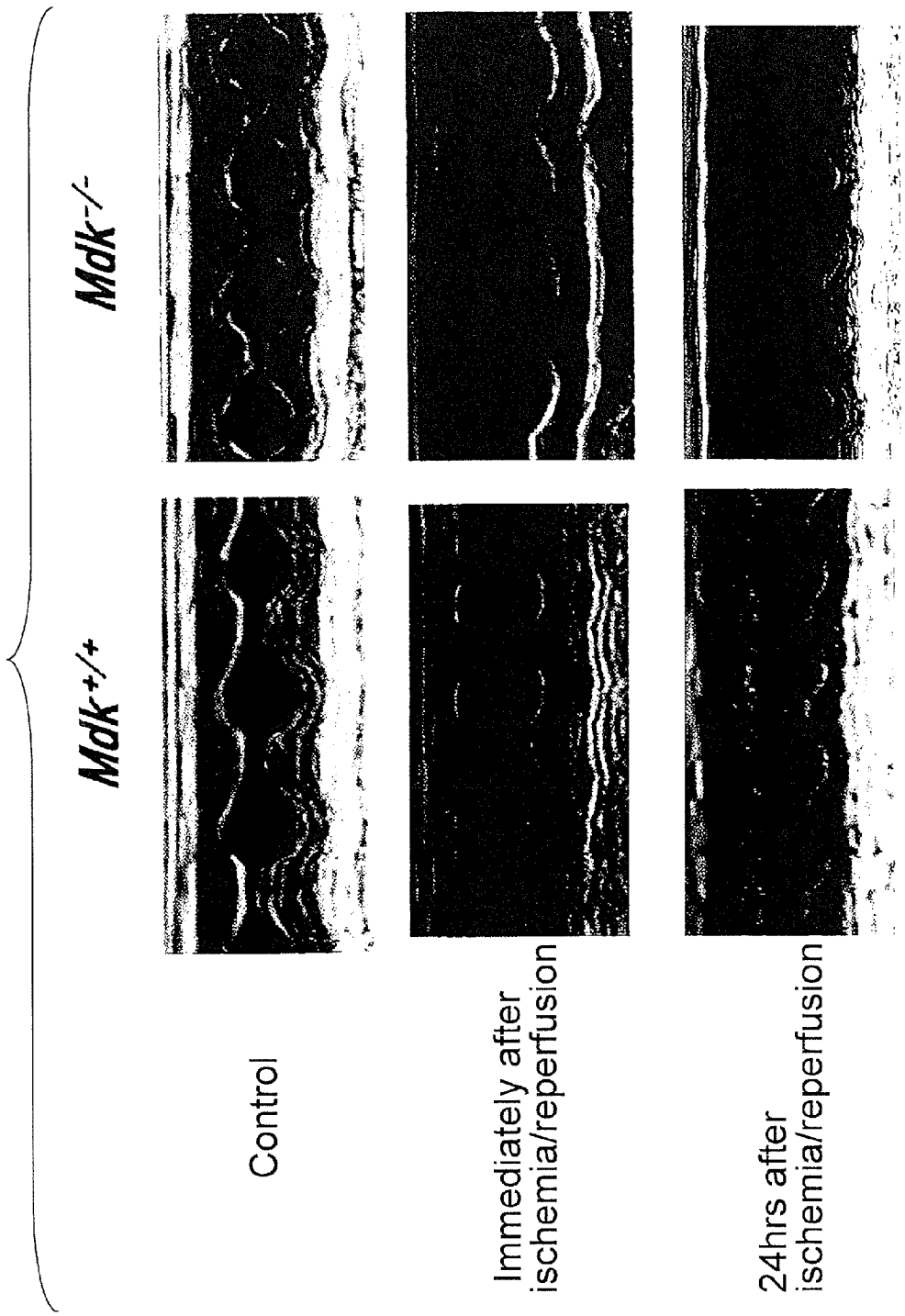
FIG. 3 shows echocardiograms of the left ventricles of mice. In order from the top: control, immediately after ischemia/reperfusion, and 24 hours after ischemia/reperfusion. Echocardiograms of Mdk$^{+/+}$ mice are on the left and those of Mdk$^{-/-}$ mice are on the right.
Figure 4:
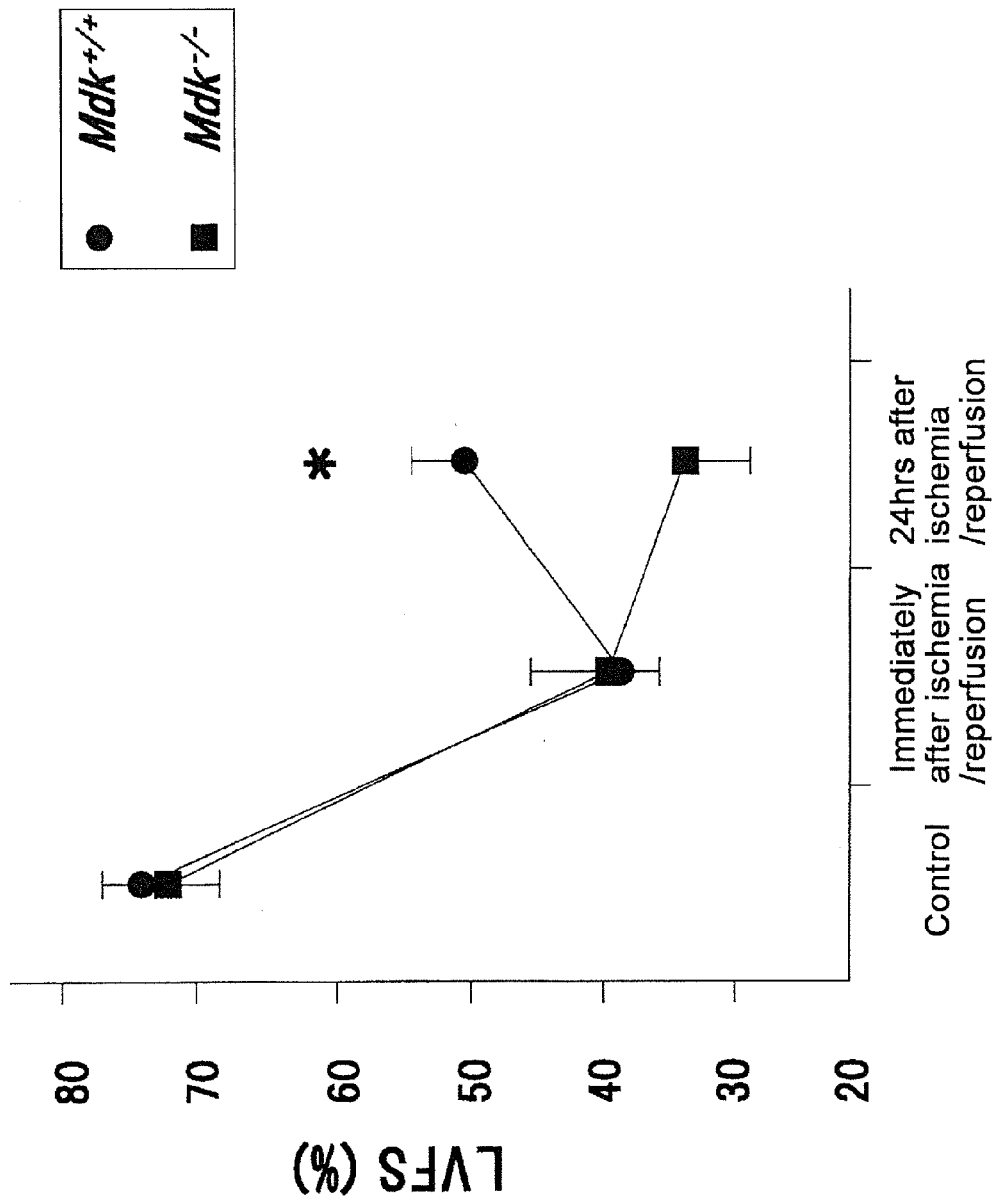
FIG. 4 is a graph showing the left ventricular fractional shortening (LVFS) changes at each stage. n=10, respectively. *P<0.01.
Figure 5:
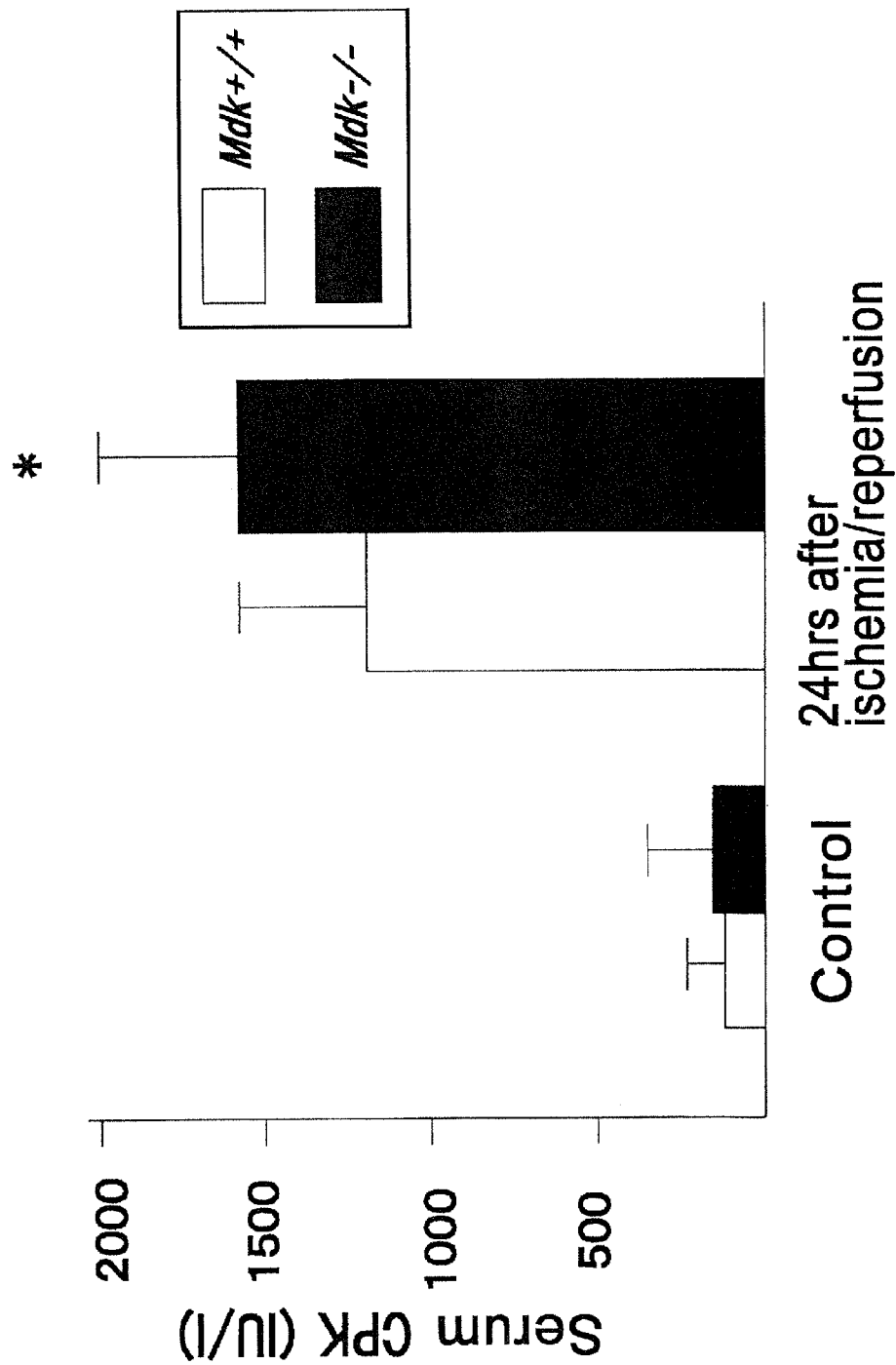
FIG. 5 is a graph showing variations in serum CPK. n=10, respectively. *P<0.01.

Morphological changes and left ventricular fractional shortening (LVFS) were examined for $Mdk^{+/+}$ mice and $Mdk^{-/-}$ mice. FIG. 3 shows the result of echocardiography on the left ventricular function, and the photographs correspond in order from the top to those of the control, immediately after ischemia/reperfusion, and 24 hours after ischemia/reperfusion. FIG. 4 is a graph showing the changes in LVFS at each stage, and FIG. 5 is a graph showing the variation in serum CPK.

Between $Mdk^{+/+}$ mice and $Mdk^{-/-}$ mice, a significant difference was not observed in the controls (before surgery) (top row in FIG. 3). Immediately after ischemia/reperfusion, the left ventricles were enlarged and LVFS decreased, but marked differences were not observed in both groups (middle row of FIG. 3). At 24 hours after ischemia/reperfusion, the LVFS in $Mdk^{-/-}$ mice was significantly smaller than in $Mdk^{+/+}$ mice (bottom row of FIG. 3, and FIG. 4). There were no significant differences in serum CPK levels between $Mdk^{+/+}$ mice and $Mdk^{-/-}$ mice in sham operations; however, 24 hours after ischemia/reperfusion, the serum CPK levels for $Mdk^{-/-}$ mice was higher than that of $Mdk^{+/+}$ mice (FIG. 5).

Figure 6:
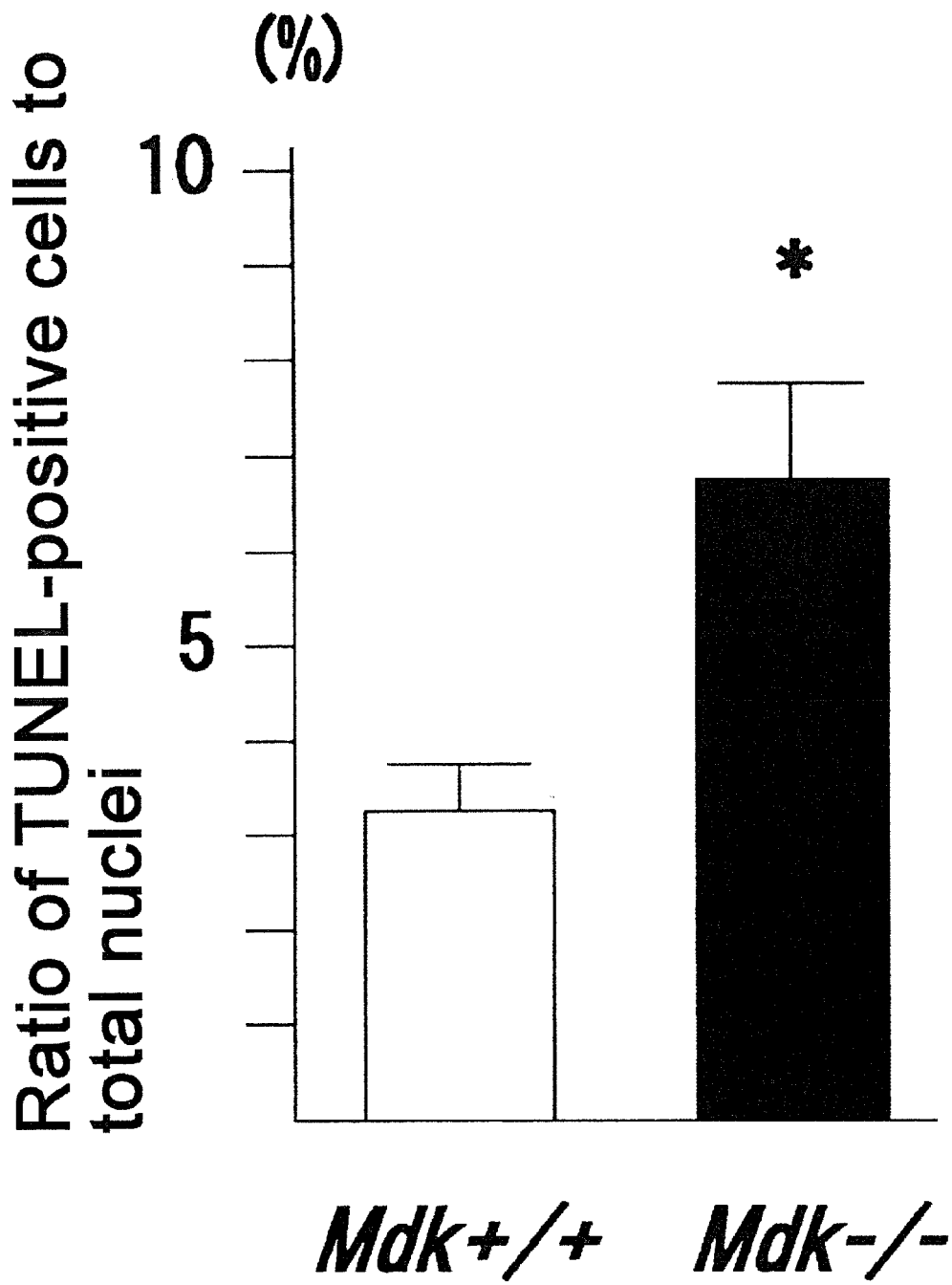
FIG. 6 is a graph showing the ratio of TUNEL-positive cells to Hoechst 33342-stained cells (total number of nuclei). Apoptotic cell densities in the peri-infarct region were compared.

Next, apoptotic cell densities in the peri-infarct region in $Mdk^{+/+}$ mice and $Mdk^{-/-}$ mice were compared. The left ventricular sections of $Mdk^{+/+}$ mice and $Mdk^{-/-}$ mice were each stained with Hoechst 33342 (for nuclear staining), and also by TUNEL staining (which stains killed cells). FIG. 6 is a graph indicating the ratios of TUNEL-positive cells to Hoechst 33342-stained cells (total number of nuclei). The cardiac sections obtained from the peri-infarct regions in $Mdk^{-/-}$ mice clearly had more TUNEL-positive cells compared to $Mdk^{+/+}$ mice (FIG. 6).

40% of $Mdk^{-/-}$ mice died within 24 hours after ischemia/reperfusion, but 90% of $Mdk^{+/+}$ mice survived this period (data not shown). As a result of autopsy, critical morphological features caused by apoptosis were found in the myocardia of $Mdk^{-/-}$ mice that died within 24 hours after ischemia/reperfusion (3 out of 8 mice).

Example 3

Evaluation of Cardioprotection by MK Protein (In Vitro Experiment)

Figure 7:
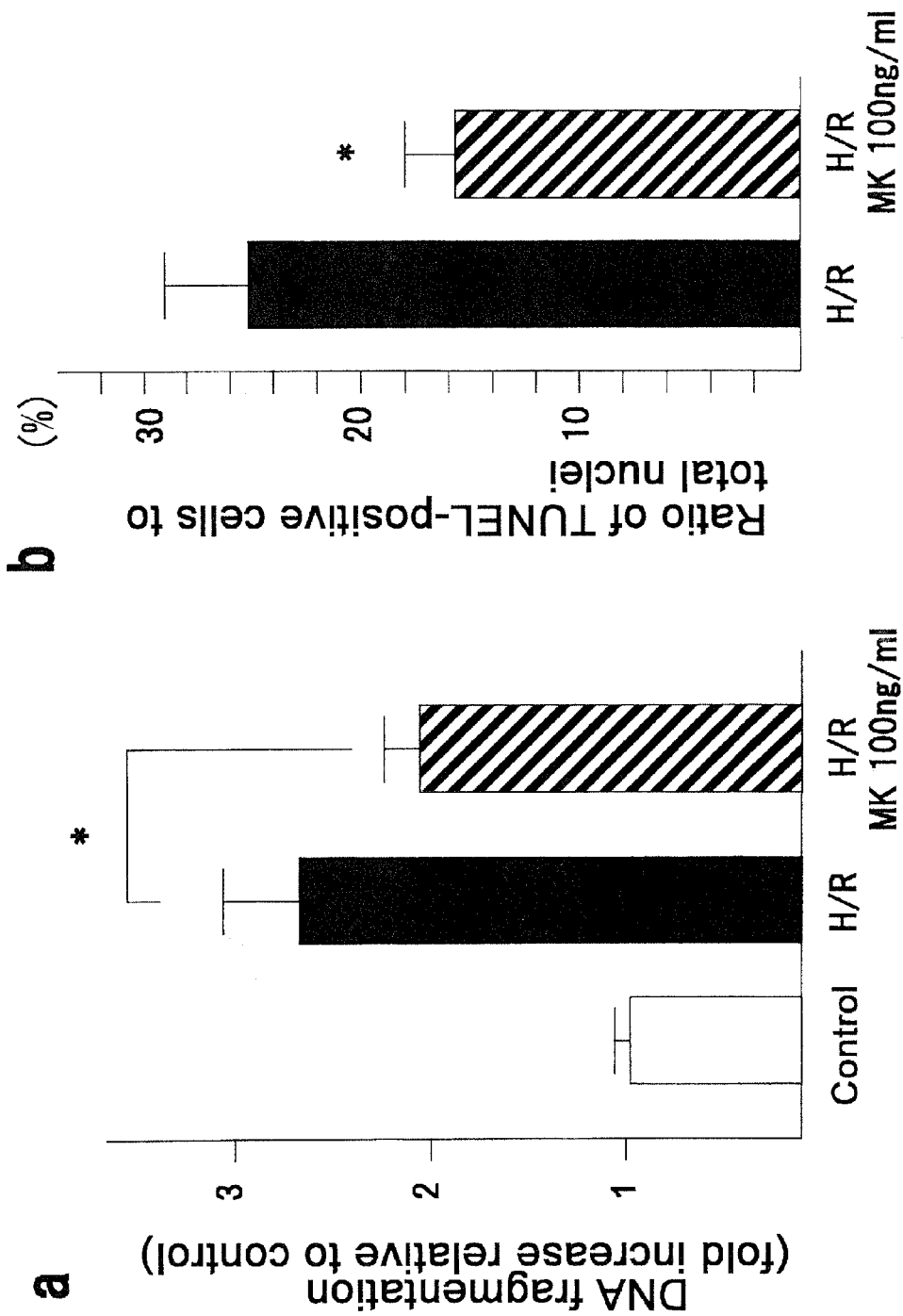
FIG. 7 (b) is a graph showing the same anti-apoptotic effect of MK protein. The effect is expressed as ratios of the number of TUNEL-positive cells to that of nuclei. *P<0.05.
Figure 8:
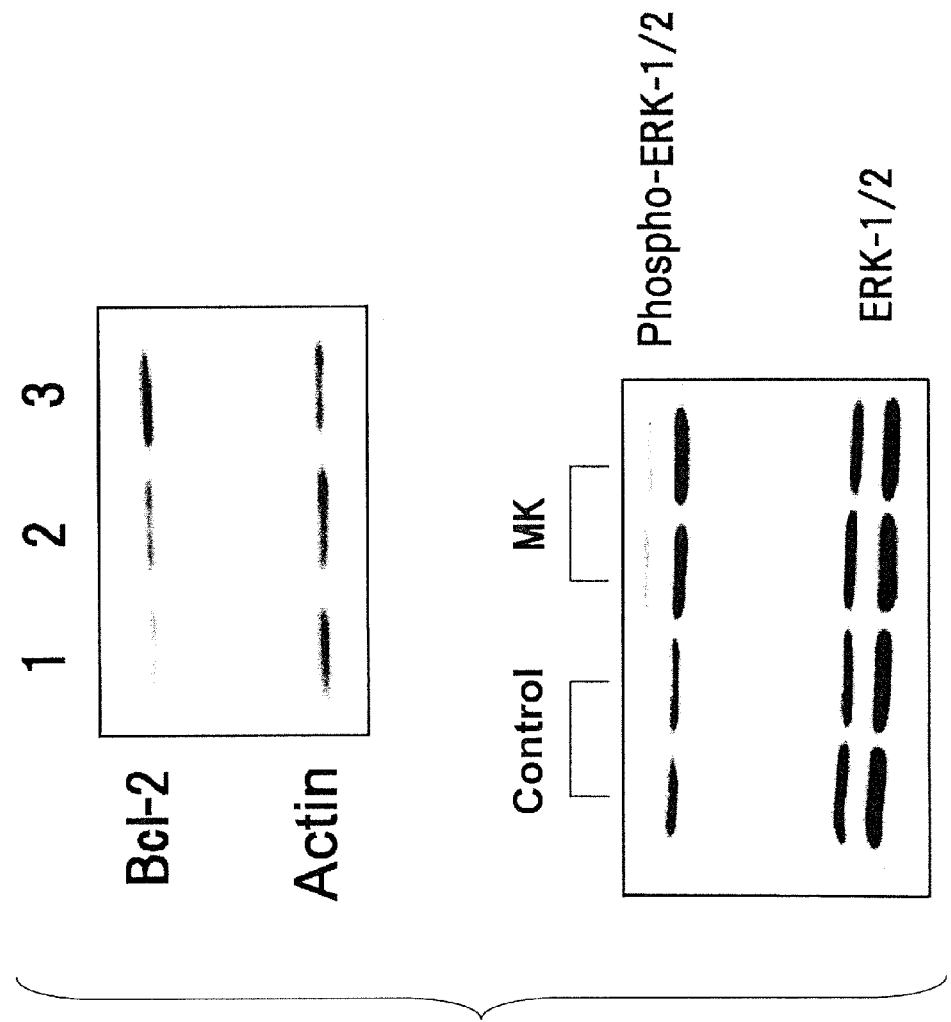
FIG. 8 (top) is an electropherogram showing the anti-apoptosis effect of MK protein. Shows the changes in Bcl-2 expression in cardiomyocytes detected by Western blotting. Lane 1: control; lane 2: cells subjected to H/R treatment (without MK addition); and lane 3: cells subjected to H/R treatment (with 100 ng/ml of MK protein).

Since apoptotic cell death of cultured cardiomyocytes is caused by hypoxia/reoxygenation (H/R), this method was used to evaluate the cardioprotective effect of MK. The cardioprotective effects of the MK protein on cultured cardiomyocytes subjected to H/R treatment are shown in FIGS. 7 and 8. FIG. 7 (a) shows the quantitative DNA fragmentation data determined by ELISA, and (b) shows the number of TUNEL-positive cells relative to the number of nuclei. FIG. 8 (top) shows the changes in Bcl-2 expression level in cardiomyocytes detected by Western blotting. Lane 1: the control, lane 2: the cells subjected to H/R treatment (without MK addition), and lane 3: the cells subjected to H/R treatment (with 100 ng/ml of MK protein).

After H/R treatment, the amount of DNA fragmentation determined by ELISA and the number of TUNEL-positive cells were both decreased significantly in the presence of 100 ng/ml of MK (FIG. 7). Bcl-2 expression level in the cardiac muscle after reoxygenation was not significantly different between the control and the cells subjected to H/R treatment (without MK addition), but increased when treated with 100 ng/ml of MK (FIG. 8 top).

Since there are reports that ERK activation is related to cardiomyocyte protection, ERK-1/2 activation in cultured cardiomyocytes was investigated. FIG. 8 (bottom) is an electropherogram showing ERK-1/2 activation by MK in cultured cardiomyocytes, and the activation (upper bands) was detected using an anti-phospho-ERK-1/2 antibody. Under serum-starved conditions, the phosphorylation level of ERK-1/2 was low, but the addition of 100 ng/ml of MK significantly increased the phosphorylated ERK-1/2. The total amount of ERK-1/2 protein was similar in both groups (lower bands).

Example 4

Evaluation of Cardioprotection by MK Protein (In Vivo Experiment: Acute Stage Model)

Figure 9:
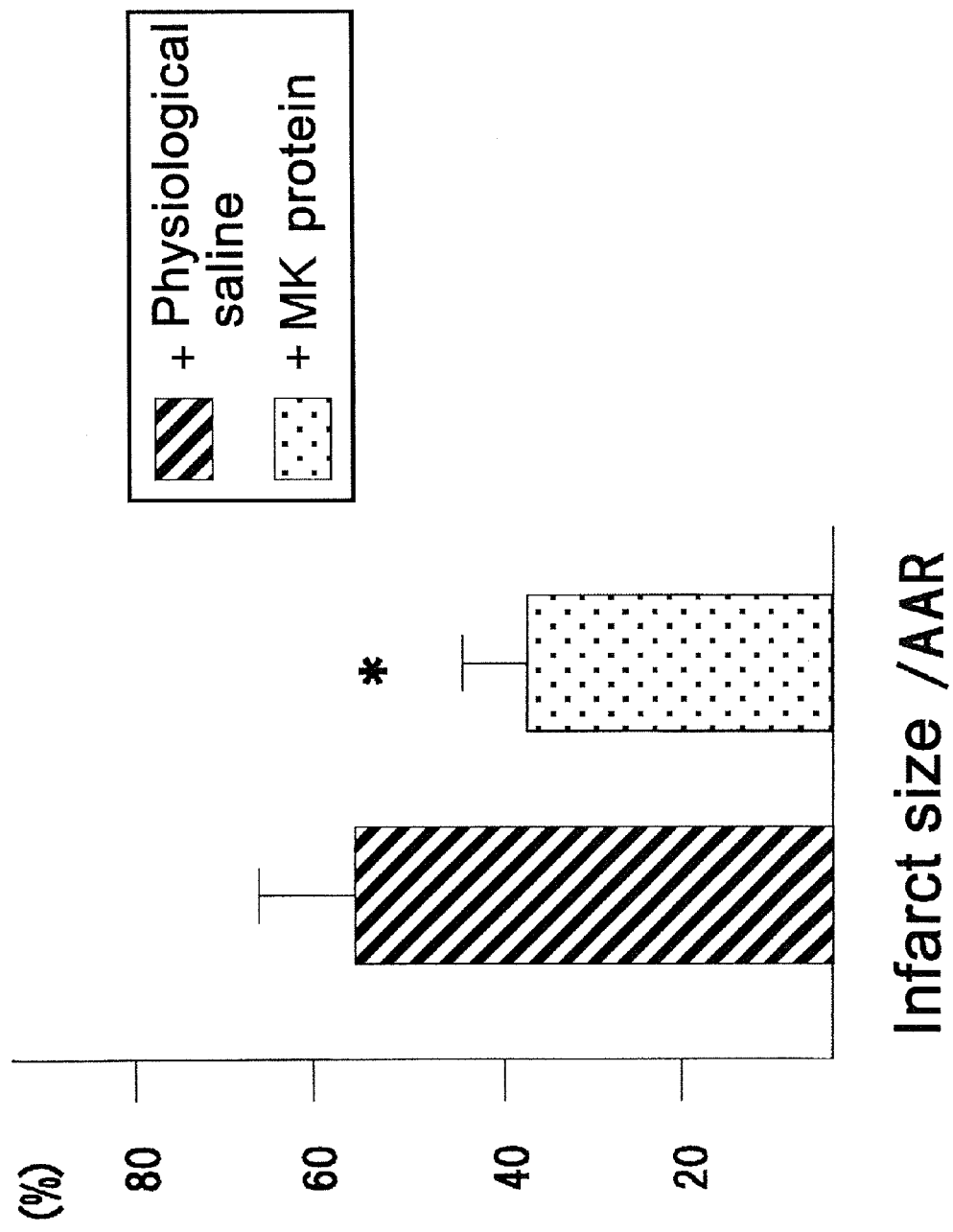
FIG. 9 is a graph showing the infarct size of the left ventricle when the MK protein was infused into the left ventricle of Mdk$^{-/-}$ mice, and that when the MK protein was not infused, as percentages of the infarct area in the ischemic area at risk (AAR). n=7, and *P<0.05.

Using acute stage mouse models, therapeutic effects of MK on ischemia/reperfusion injuries were investigated in vivo. The coronary artery of Mdk$^{-/-}$ mice was ligated, and immediately after reperfusion, 20 µl of MK protein solution (10 µg/ml) was directly injected into the muscle of the cardiac left ventricular wall. For the control, a medium (physiological saline) without MK was injected in a similar manner. FIG. 9 is a graph that shows the infarct size of the left ventricle when the MK protein was injected into the left ventricle of Mdk$^{-/-}$ mice, and that when the MK protein was not injected, as percentages of the infarct area in the ischemic area at risk (AAR). The graph shows that 24 hours after reperfusion, the infarct size in mice to which the MK protein had been administered was significantly smaller than that in the control mice to which the MK protein had not been administered.

Example 5

Evaluation of Cardioprotection by MK Protein (In Vivo Experiment: Chronic Stage Model)

Using chronic stage mouse models, therapeutic effects of MK on ischemia/reperfusion injuries were investigated in vivo. The coronary artery of Mdk$^{+/+}$ mice or Mdk$^{-/-}$ mice was ligated, and conditions of these mice were followed up for two weeks after reperfusion. At the beginning of observation, the Mdk$^{-/-}$ mice were divided into two groups, and for one of them ALZET micro-osmotic pump (Model 1002) loaded with 90 µl of MK protein solution (0.8 mg/ml) was subcutaneously implanted in the abdomen, and MK protein was continuously administered by an osmotic pressure pump. FIG. 10 shows the mortality rates and the heart/body weight ratios in chronic stage models. Compared to the Mdk$^{+/+}$ mice (top row), the mortality rate significantly increased in Mdk$^{-/-}$ mice (middle row); however, continuous administration of the MK protein improved the mortality rate to the same level as that of Mdk$^{+/+}$ mice (bottom row). The heart/body weight ratio, one of the indicators of heart failure, tended to increase in Mdk$^{-/-}$ mice (middle row) than in Mdk$^{+/+}$ mice (top row); however, continuous administration of the MK protein improved the heart/body weight ratio to the same level as that of Mdk$^{+/+}$ mice (bottom row).

Figure 11:
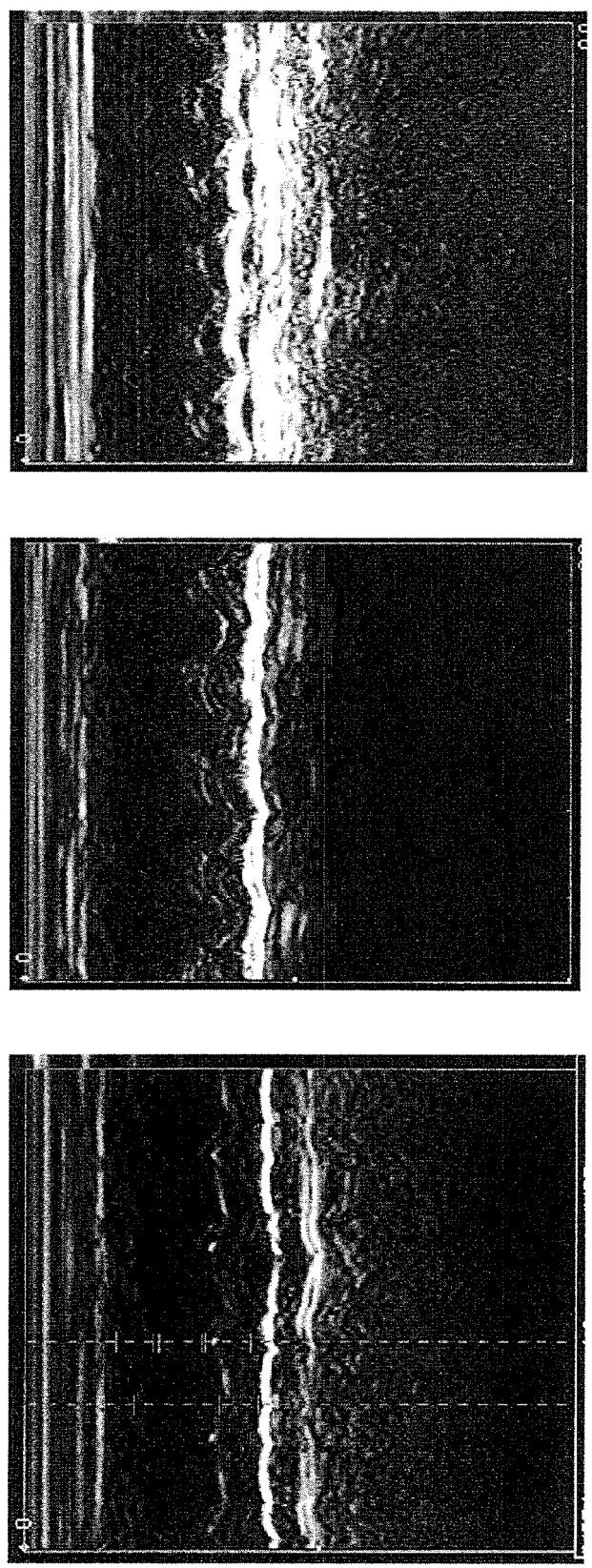
FIG. 11 shows the echocardiograms of the left ventricle of mice. In order from the left, the echocardiograms of Mdk$^{+/+}$ mouse, Mdk$^{-/-}$ mouse, and Mdk$^{-/-}$ mouse to which MK protein was continuously administered are shown.
Figure 12:
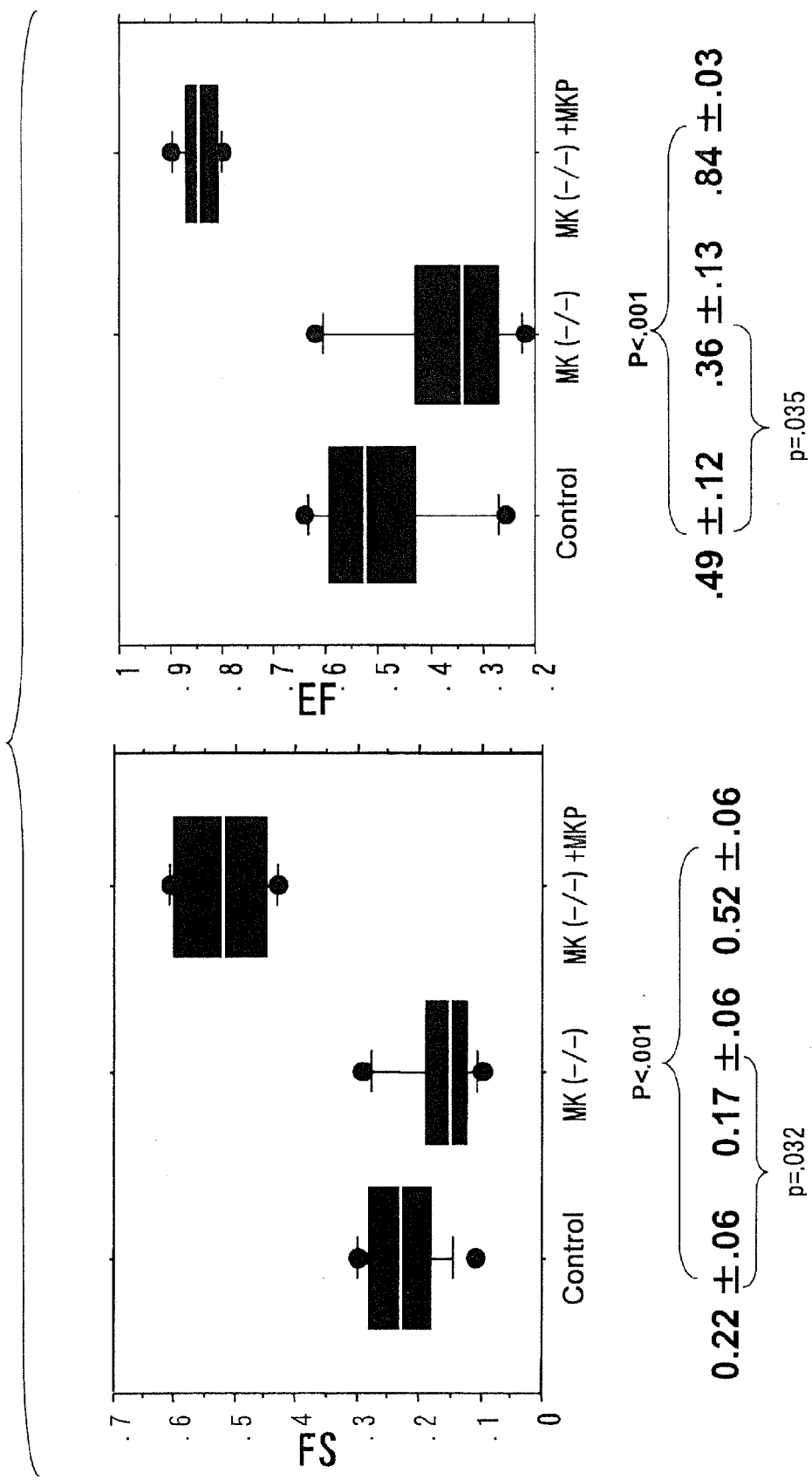
FIG. 12 shows graphs that summarize the change in LVFS and left ventricular ejection fraction (LVEF) at each stage.

Morphological changes and left ventricular fractional shortening (LVFS), left ventricular ejection fraction (LVEF), and IVSTs/d (left ventricular wall thickness) were examined for Mdk$^{+/+}$ mice and Mdk$^{-/-}$ mice. FIG. 11 shows the evaluation of left ventricular function by the echocardiography for Mdk$^{+/+}$ mice, Mdk$^{-/-}$ mice, and Mdk$^{-/-}$ mice to which the MK protein had been continuously administered, in order from the left. FIG. 12 shows graphs indicating the change in LVFS and LVEF at each stage.

The echocardiography results revealed that the cardiac function of Mdk$^{-/-}$ mice was significantly decreased compared to that of Mdk$^{+/+}$ mice, but prominently improved by continuous administration of MK protein (FIGS. 11 and 12).

Figure 13:
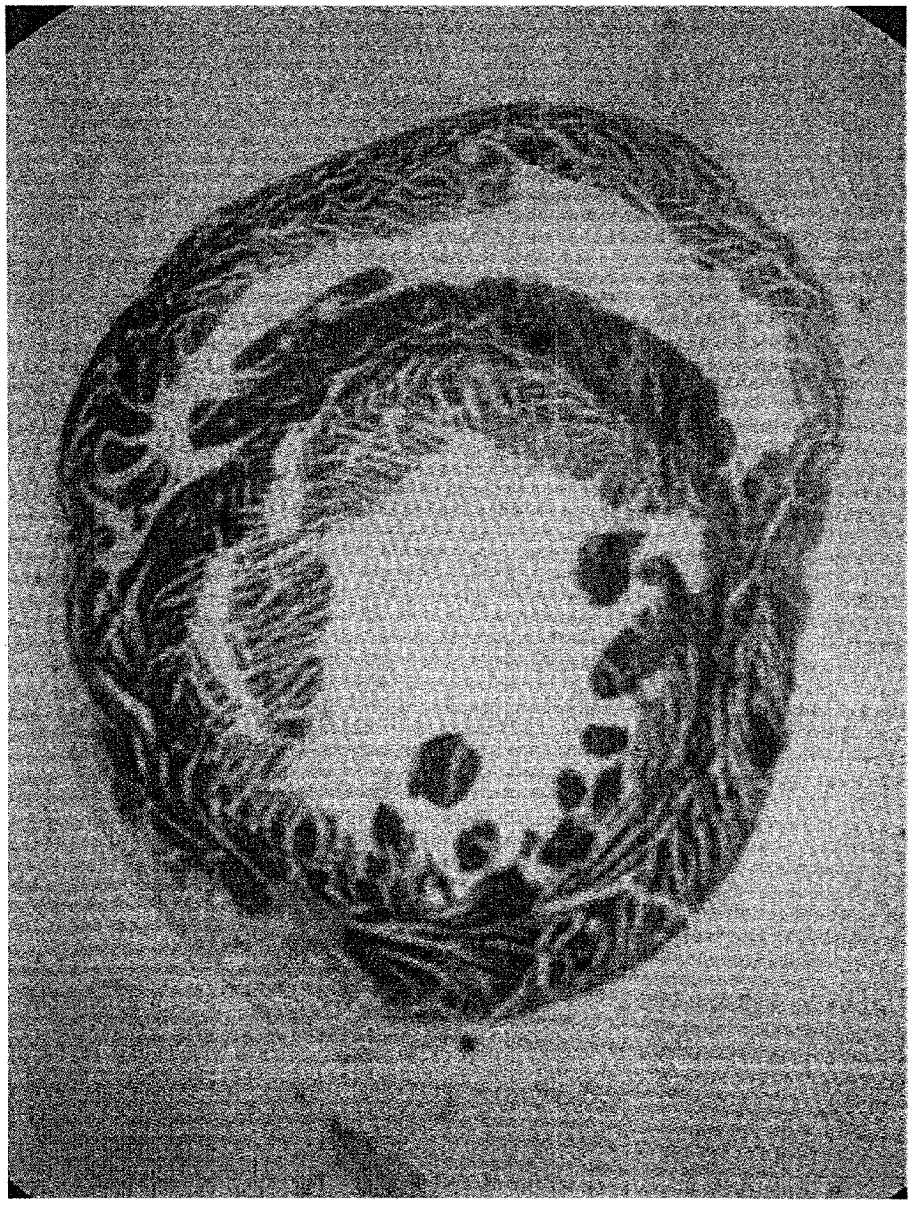
FIG. 13 shows the image of a stained cardiac slice of a wild-type mouse (Mdk$^{+/+}$ mouse) two weeks after reperfusion.
Figure 14:
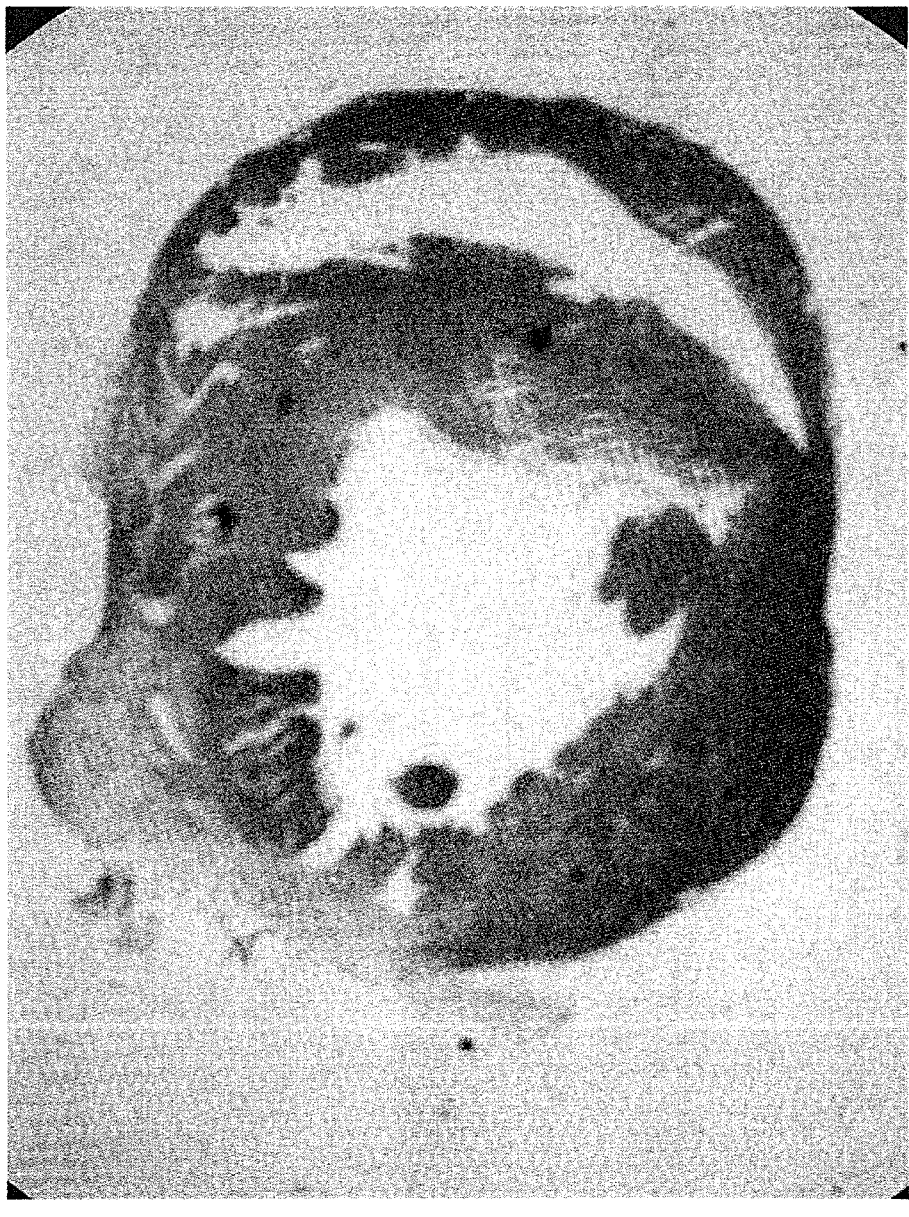
FIG. 14 shows the image of a stained cardiac slice of an Mdk$^{-/-}$ mouse two weeks after reperfusion.
Figure 15:
FIG. 15 shows the image of a stained cardiac slice of an Mdk$^{-/-}$ mouse to which MK protein was administered continuously for two weeks after reperfusion.

Next, histopathological examination was conducted on Mdk$^{+/+}$ mice (FIG. 13), Mdk$^{-/-}$ mice (FIG. 14), and Mdk$^{-/-}$ mice to which MK protein was continuously administered (FIG. 15). As a result, the fibrosis area in the cardiac muscle increased in Mdk$^{-/-}$ mice than in Mdk$^{+/+}$ mice, but was found to be improved by continuous administration of the MK protein.

INDUSTRIAL APPLICABILITY

The present invention enables treatment or prevention of myocardial damage or heart failure using pharmaceutical compositions, and treatment or prevention of myocardial damage or heart failure without performing heart surgery, a procedure that has donor availability and histocompatibility issues.

The invention claimed is:

1. A method to reduce loss in cardiac function in a subject during a chronic stage following ischemia/reperfusion, which method comprises administering to a subject that has suffered the ischemia/reperfusion an effective amount of Midkine continuously for up to two weeks following the ischemia/reperfusion, to reduce the loss in cardiac function in the chronic stage following ischemia/reperfusion.

2. The method of claim 1 wherein the subject is human.

3. The method according to claim 1, wherein the continuous administration of Midkine for up to two weeks following the ischemia/reperfusion improves cardiac function as determined by echocardiography.

4. The method according to claim 1, wherein the continuous administration of Midkine for up to two weeks following the ischemia/reperfusion improves cardiac function as determined by increased left ventricular fractional shortening (LVFS).

5. The method according to claim 1, wherein the continuous administration of Midkine for up to two weeks following the ischemia/reperfusion improves cardiac function as determined by increased left ventricular ejection fraction (LVEF).

6. The method according to claim 1, wherein the continuous administration of Midkine for up to two weeks following the ischemia/reperfusion improves cardiac function as determined by left ventricular wall thickness (IVSTs/d).

7. The method according to claim 1, wherein the continuous administration of Midkine for up to two weeks following the ischemia/reperfusion improves cardiac function as determined by fibrosis in cardiac muscle.

* * * * *